Figure 1A:
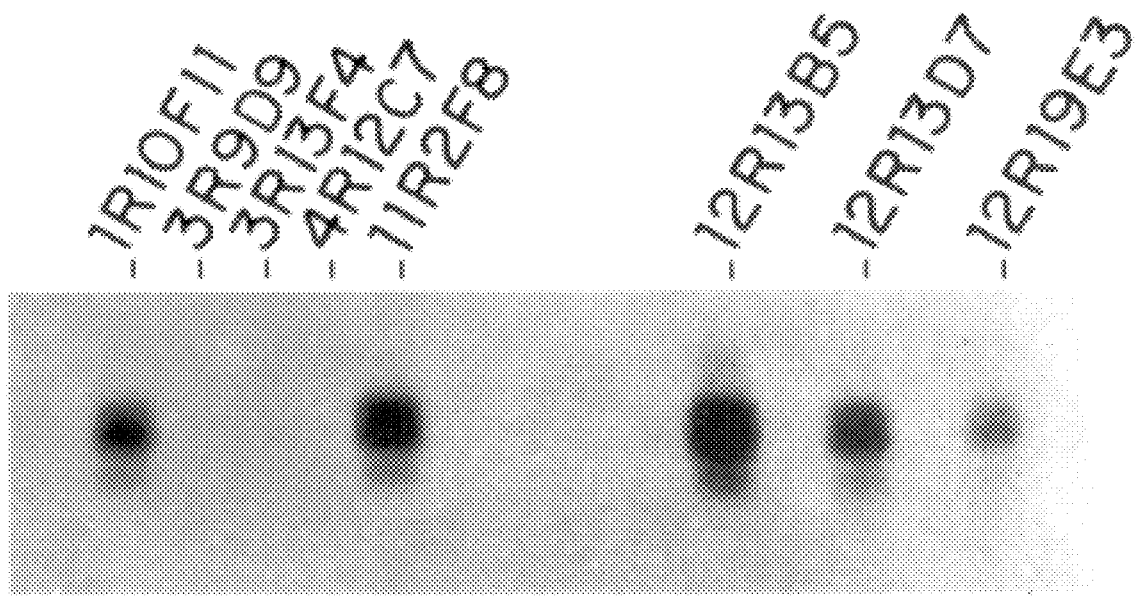

United States Patent [19]
Radka et al.

[11] Patent Number: 5,907,033
[45] Date of Patent: *May 25, 1999

[54] ANTI-ONCOSTATIN M MONOCLONAL ANTIBODIES

[75] Inventors: Susan F. Radka; Peter S. Linsley; Mohammed Shoyab, all of Seattle, Wash.

[73] Assignee: Bristol-Myers Squibb Co., New York, N.Y.

[ * ] Notice: This patent is subject to a terminal disclaimer.

[21] Appl. No.: 08/678,922

[22] Filed: Jul. 12, 1996

Related U.S. Application Data

[63] Continuation of application No. 07/943,387, Sep. 10, 1992, Pat. No. 5,681,930, which is a continuation of application No. 07/664,191, Mar. 4, 1991, abandoned, which is a continuation-in-part of application No. 07/501,824, Mar. 29, 1990, abandoned, which is a continuation-in-part of application No. 07/144,574, Jan. 15, 1988, which is a continuation-in-part of application No. 07/046,846, May 4, 1987, Pat. No. 5,120,535, which is a continuation-in-part of application No. 06/935,283, Nov. 26, 1986, abandoned, which is a continuation-in-part of application No. 06/811,235, Dec. 20, 1985, abandoned.

[51] Int. Cl.$^6$ .............................. C07K 16/24; C12N 5/06
[52] U.S. Cl. ................................ 530/388.23; 530/388.24; 435/335; 435/336
[58] Field of Search ........................ 530/388.24, 388.23; 435/335, 336

[56] References Cited

FOREIGN PATENT DOCUMENTS

| 0 290 948 | 11/1988 | European Pat. Off. . |
| 2185485 | 7/1987 | United Kingdom . |

OTHER PUBLICATIONS

Benjamin et al., 1984, "The Antigenic Structure of Proteins: A Reappraisal", Ann. Rev. Immunol. 2:67–101.
Boscato and Stuart, 1988, "Heterophilic Antibodies: A Problem for All Immunoassays", Clin. Chem. 34: 27–33.
Brown et al., 1987, "Purification and Characterization of Cytostatic Lymphokines Produced by Activated Human T Lymphocytes", J. Immunol. 139:2977–2983 (Brown I).
Brown et al., 1988, "Oncostatin M Differentially Regulates the Action of Type I Transforming Growth Factor–β", J. Cell. Biochem. Suppl. 0 (12 Part A):194 (Brown II).
Brown et al., 1989, "Oncostatin M as a Unique Modulator of Endothelial Cell Surface Properties", J. Cell. Biochem. Suppl. 0 (13 Part E):189 (Brown III).
Brown et al., 1990, *Molecular Biology of the Cardiovascular System*, Proceedings of a UCLA Symposium held at Keystone, Co on Apr. 10–17, 1989, Roberts et al., ed., Alan R. Liss, Inc., NY, pp. 195–206 (Brown IV).
Cebrian et al., 1987, "Different Functional Sites on RIFN–o2 and their Relation to the Cellular Receptor Binding Site", J. Immunol. 138:484–490.
Cunningham and Wells, 1989, "High–Resolution Epitope Mapping of hGH–Receptor Interactions by Alanine–Scanning Mutagenesis", Science 244:1081–1085.

Gaulton and Greene, 1986, "Idiotypic Mimicry of Biological Receptors", Ann. Rev. Immunol. 4:253–280.
Gunderson et al., 1988, "Expression of Oncostatin M and Properties of the Recombinant Protein", J. Cell. Biochem. Suppl. 0 (12 Part A):224.
Harris and Emery, 1993, "Therapeutic Antibodies –the Coming of Age", TIBTECH 11:42–44.
Kadin et al., 1982, *Antibody as a Tool*, Marchalonis et al., eds., John Wiley & Sons NY, pp. 447–484.
Kato et al., 1979,"Use of Antibody Fab' Fragments to Remove Interference by Rhuematoid Factors with the Enzyme–Linked Sandwich Immunoassay", FEBS Lett. 102:253–256.
Linsley et al., 1988, "Identification of a Membrane Receptor for the Growth Regulator, Oncostatin M", J. Cell. Biochem. Suppl. 0 (12 Part A):227 (Linsley I).
Linsley et al., 1989, "Identification and Characterization of Cellular Receptors for the Growth Regulator, Oncostatin M", J. Biol. Chem. 264:4282–4289.
Linsley et al., 1990, "Cleavage of a Hydrophilic C–Terminal Domain Increases Growth–Inhibitory Activity of Oncostatin M", Mol. Cell. Biol. 10:1882–1890 (Linsley II).
Malik et al., 1989, "Molecular Cloning, Sequence Analysis, and Functional Expression of a Novel Growth Regulator, Oncostatin M", Mol. Cell. Biol. 9:2847–2853.
Porter, 1991, "The Prospects for Therapy with Tumor Necrosis Factors and their Antagonists", TIBTECH 9:158–162.
Redlich and Grossberg, 1989, "Analysis of Antigenic Domains on Natural and Recombinant Human IFN–y by the Inhibition of Biologic Activities with Monoclonal Antibodies", J. Immunol. 143:1887–1893.
Schreiber et al., 1980, "Anti–Alprenolol Anti–Idiotypic Antibodies Bind to β–Adrenergic Receptors and Modulate Catecholamine–Sensitive Adenylate Cyclase", Proc. Natl. Acad. Sci. USA 77:7385–7389.
Sege and Peterson, 1978, "Use of Anti–Idiotypic Antibodies as Cell–Surface Receptor Probes", Proc. Natl. Acad. Sci. USA 75:2443–2447.
Vaux et al., 1990, "Identification by Anti–Idiotypic Antibodies of an Intracellular Membrane Protein that Recognizes a Mammalian Endoplasmic Reticulum Retention Signal", Nature 345:495–502.
Zarling et al., 1986, "Oncostatin M: A Growth Regulator Produced by Differentiated Histiocytic Lymphoma Cells", Proc. Natl. Acad. Sci. USA 83:9739–9743.

*Primary Examiner*—Michael P. Woodward
*Attorney, Agent, or Firm*—Pennie & Edmonds LLP

[57] ABSTRACT

The present invention relates to monoclonal antibodies that define Oncostatin M, a novel cytokine. The monoclonal antibodies of the invention are capable of binding to Oncostatin M, inhibiting Oncostatin M receptor binding, and/or inhibiting Oncostatin M bioactivity. Such antibodies may be used to detect the presence at Oncostatin M and/or to modulate Oncostatin M bioactivities in an in vivo or in vitro system.

24 Claims, 5 Drawing Sheets

ANTI-ONCOSTATIN M MONOCLONAL ANTIBODIES

This is a continuation of application Ser. No. 07/943,387, filed Sep. 10, 1992 now U.S. Pat. No. 5,681,930 and allowed on Dec. 13, 1995, which is a continuation of application Ser. No. 07/664,191, filed Mar. 4, 1991, now abandoned, which is a continuation-in-part of application Ser. No. 07/501,824 filed Mar. 29, 1990, abandoned, which is a continuation-in-part of application Ser. No. 07/144,574, filed Jan. 15, 1988 which is a continuation-in-part of application Ser. No. 07/046,846, filed May 4, 1987, now U.S. Pat. No. 5,120,535 which is a continuation-in-part of application Ser. No. 06/935,283, filed Nov. 26, 1986, abandoned which is a continuation-in-part of application Ser. No. 06/811,235, filed Dec. 20, 1985, abandoned each of which is incorporated by reference herein in its entirety.

TABLE OF CONTENTS

1. Introduction
2. Background Of The Invention
3. Summary Of The Invention
    3.1. Definitions
4. Brief Description of the Figures
5. Detailed Description of the Invention
    5.1. Characteristics Of Monoclonal Antibodies Defined By Their Specificity For Oncostatin M
        5.1.1. Oncostatin M Antigen Recognition
        5.1.2. Inhibition Of Oncostatin M Activity
        5.1.3. Inhibition Of Binding To Oncostatin M Receptor
    5.2. Methods for Preparing Monoclonal Antibodies to Oncostatin M
    5.3. Uses of Monoclonal Antibodies to Oncostatin M
        5.3.1. Generation of Anti-Idiotypes that Mimic the Effects of Oncostatin M
        5.3.2. Oncostatin M Epitope Mapping
6. Example: Production of Monoclonal Antibodies to Oncostatin M
    6.1. Materials and Methods
        6.1.1. Immunization and Fusion
        6.1.2. Enzyme-linked Immunoassays
        6.1.3. Immunoprecipitation
        6.1.4. Growth Inhibitory Assay
        6.1.5. Oncostatin M Radio-receptor Assay
        6.1.6. Oncostatin M Mutants
        6.1.7. Detection of Oncostatin M in Serum with Monoclonal Antibodies
    6.2. Results
        6.2.1. Selection of Monocolonal Antibodies with Specificity for Oncostatin M
        6.2.2. Monoclonal Antibodies Immunoprecipitate with Oncostatin M
        6.2.3. Monoclonal Antibodies that Neutralize Oncostatin M in the Growth Inhibition Assay
        6.2.4. Moncolonal Antibodies that Inhibit Binding of Oncostatin M in the Radio-receptor Assay
    6.3. Analysis of Functional Sites and Epitope Mapping of Oncostatin M
        6.3.1. Mapping of OM Epitopes by EIA on Oncostatin M Mutants
        6.3.2. Serological Analysis of OM1 and OM2 Epitopes
7. Deposit of Microorganisms

1. INTRODUCTION

The present invention relates to anti-Oncostatin M monoclonal antibodies. The antibodies of the invention are characterized as being capable of binding to-Oncostatin M, inhibiting Oncostatin M receptor binding and/or inhibiting Oncostatin M bioactivity. The monoclonal antibodies of the present invention may be used to detect the presence of Oncostatin M and/or to modulate Oncostatin M biological activities in an in vivo or in vitro system.

2. BACKGROUND OF THE INVENTION

It is now well recognized that somatic cell hybrids are an important source of specific cellular products that cannot be obtained from short-term primary cultures. The best example of this is the system developed by Milstein and others for the production of hybrid myelomas making monoclonal antibody against an antigen of choice (Kohler and Milstein, 1975, Nature (London) 256:495; Galfre et al., 1977, Nature (London) 266:550). Such hybrids provide a constant supply of monoclonal antibody against specific antigens. These antibodies can be used as reagents for any procedures for which antibodies were previously used, but with the added advantage of higher levels of discrimination, lower background and a continuous available supply of the antibodies.

The production of monoclonal antibodies in general first involves immunization, removal of immune response cells, fusion of these cells, in for example polyethylene glycol, with constantly dividing tumor cells ("immortal") selected for their inability to secrete an immunoglobin. The resulting cells (hybridomas) are distinguished by growth in, for example, HAT (hypoxanthine, aminopterin, thymidine). Each hybridoma is the fusion product of a single-forming antibody cell and a tumor cell having the ability of the former cell to secrete a single species of antibody and the immortality of the latter cell enabling it to proliferate continuously, and provide cell progeny with an unending supply of antibody with a single specificity.

3. SUMMARY OF THE INVENTION

The present invention involves the production and use of monoclonal antibodies specific for Oncostatin M, a novel cytokine which exhibits pleiotropic effects on a wide variety of normal and transformed cells. Any monoclonal antibodies having the characteristics of the monoclonal antibodies described herein are within the scope of the present invention. For example, monoclonal or chimeric antibodies which competitively inhibit the immunospecific binding of the monoclonal antibodies described herein to their Oncostatin M epitopes and/or which modulate Oncostatin M biological activities are within the scope of the invention.

The invention is described by way of examples in which hybridoma technology is used to generate the anti-Oncostatin M antibodies of the invention, but the scope of the invention is not intended to be restricted to the use of such cell hybridization techniques. The exemplary antibodies are grouped according to whether they form immunoprecipitates with either native Oncostatin M, denatured Oncostatin M, or both. Each group is further characterized by the ability to block Oncostatin M mediated growth inhibition and/or the binding of Oncostatin M to its cell surface receptors. Such antibodies are utilized to map epitopes and functional sites of the novel Oncostatin M protein.

3.1. Definitions

The following terms, as used herein, shall have the indicated meanings:

DDEIA=double determinant enzyme-linked immunoassay

GIA=growth inhibitory assay
HRP=horseradish peroxidase
micro-EIA=micro-enzyme linked immunoassay
MAb=monoclonal antibody
OM=Oncostatin M
RRA=radioreceptor assay
OM1=1R1OF11 monoclonal antibody
OM2=11R2F8 monoclonal antibody
OM3=12R13D7 monoclonal antibody
OM4=4R112C7 monoclonal antibody
OM5=3R9D9 monoclonal antibody
OM6=3R13F4 monoclonal antibody
OM7=12R13B5 monoclonal antibody
OM8=12R19E3 monoclonal antibody

4. BRIEF DESCRIPTION OF THE FIGURES

Figure 1B:
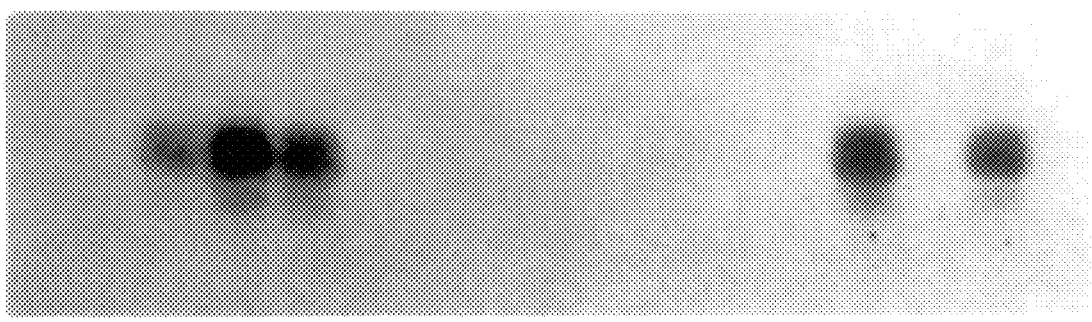

FIG. 1. Immunoprecipitation of $^{35}$S-methionine and $^{35}$S-cysteine labelled Oncostatin M from supernatants of the CHO cell line stably transfected with cDNA encoding Oncostatin M (A) Reactivity of a series of anti-Oncostatin M monoclonal antibodies with "native"0 metabolically labelled Oncostatin M (supernatant collected from metabolically labelled CHO transfectants) (B) Reactivity of these same antibodies with supernatant collected from metabolically labelled CHO cells which was denatured by treatment with SDS, 2-mercaptoethanol, and boiling prior to incubation with the monoclonal antibodies. Lane 1:negative control antibody; lane 2:OM1; lane 3:OM5; lane 4:OM6; lane 5:OM4; lane 6:OM2; lane 7:OM7; lane 8:OM3; lane 9:OM8.

FIG. 2. Examination of neutralizing activity of two different anti-Oncostatin M monoclonal antibodies in GIA of the A375 melanoma cell line: (A) activity of various concentrations of OM2; (B) activity of various concentrations of OM1.

Figure 3:
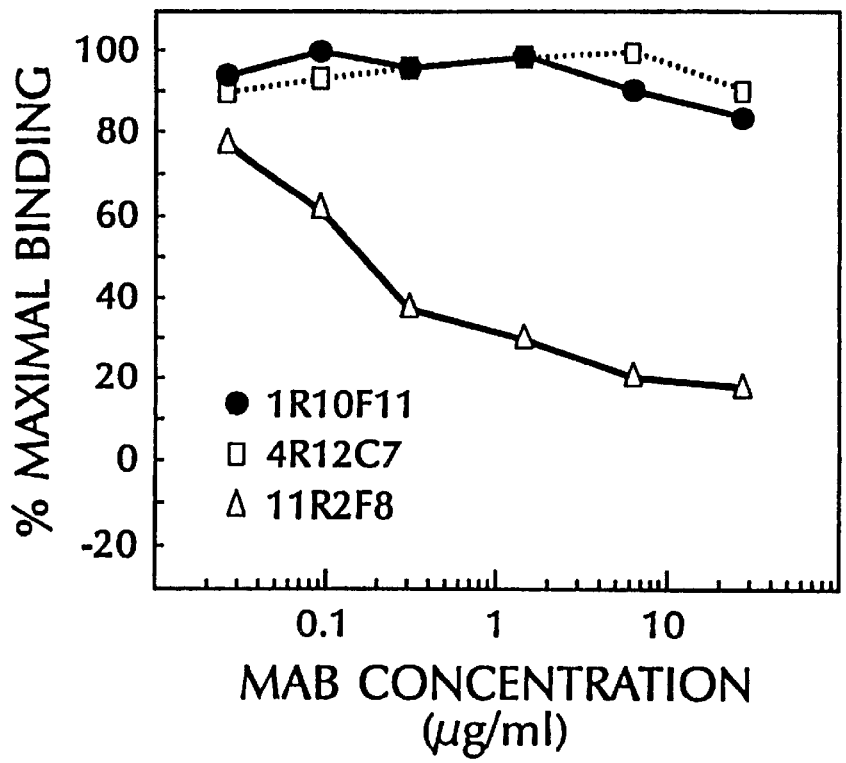

FIG. 3. Effects of several anti-Oncostatin M monoclonal antibodies on the binding of $^{125}$I Oncostatin M to the H2981 lung carcinoma cell line in the Radioreceptor assay.

Figure 4:
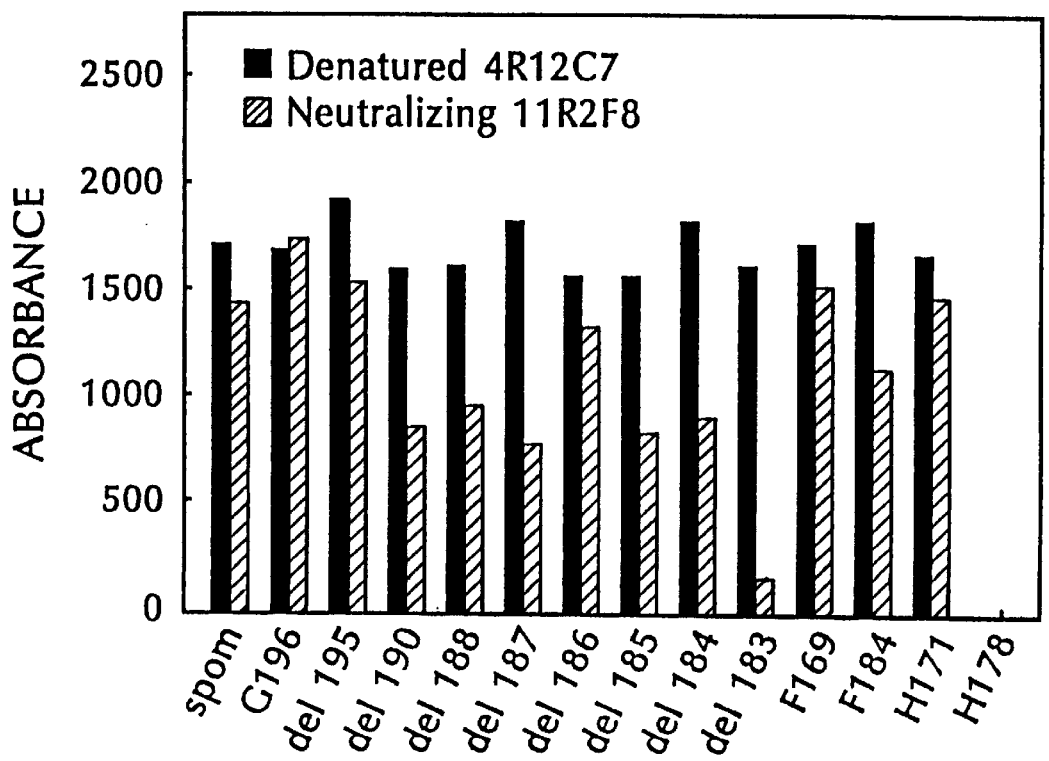

FIG. 4. Binding, as detected by EIA, of two different anti-oncostatin M monoclonal antibodies to supernatants secreted by COS cells transfected with a series of mutant Oncostatin M constructs containing amino acid deletions or alterations. Data are presented as total absorbance units at OD 460. Background binding is not subtracted. "del" indicates the most C-terminal amino acid which is deleted, while alphabetical letters indicate the amino acid alteration made.

Figure 5:
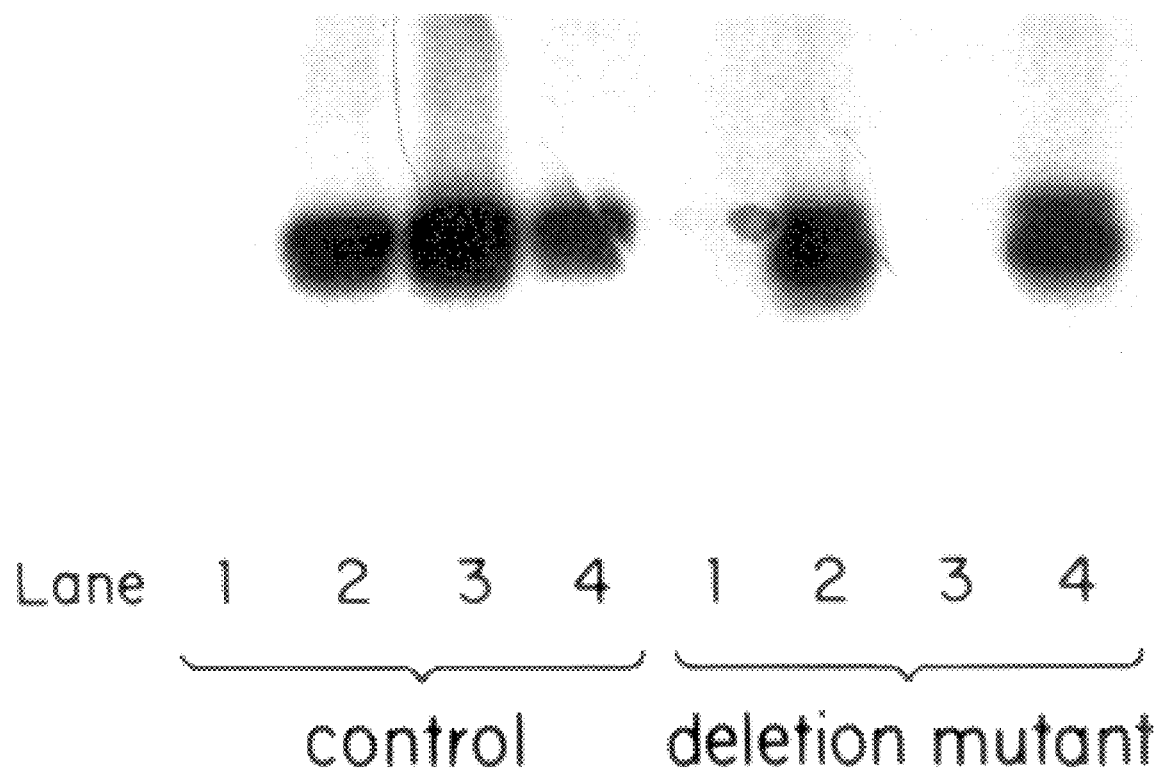

FIG. 5. Comparison of abilities of different anti-Oncostatin M monoclonal antibodies to immunoprecipitate Oncostatin M secreted by either the parental construct SPOM or the deletion mutant delta 44–47. Lane 1:negative control antibody; lane 2:OM1; lane 3:OM2; lane 4:OM3.

Figure 6:
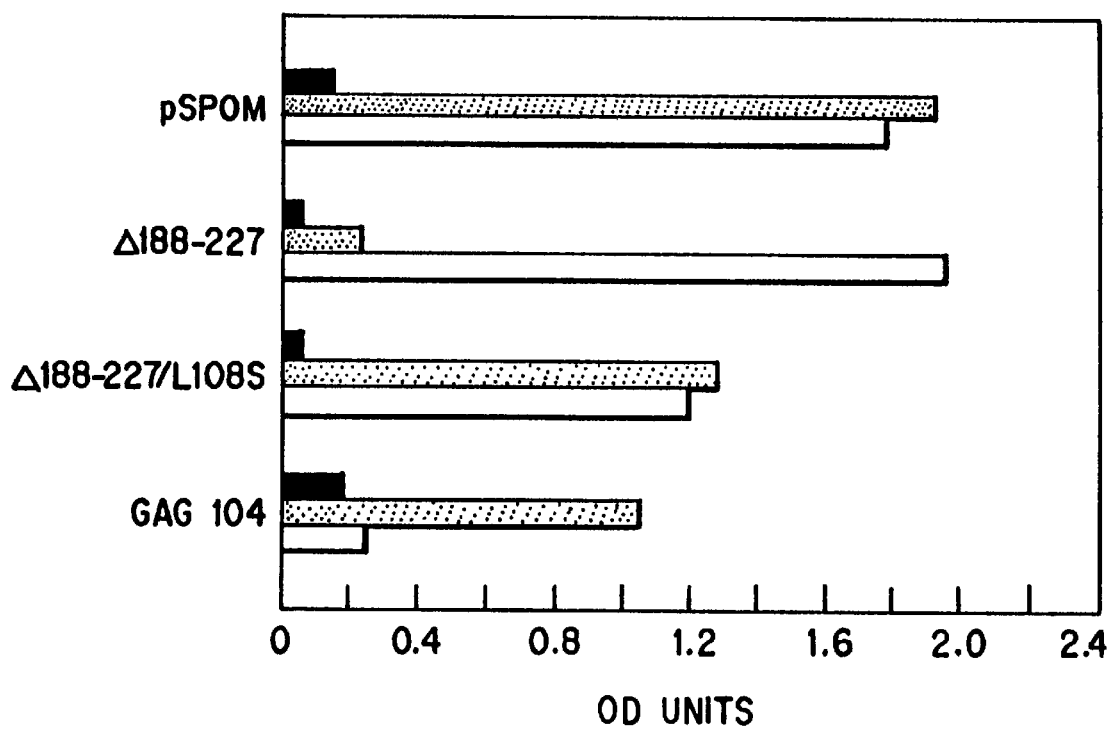

FIG. 6. Mapping of the epitopes detected by two different anti-oncostatin M monoclonal antibodies, OM3 and OM4. The relative binding, in absorbance units, of OM3 and OM4 is compared to that of a negative control antibody on OM from serum-free conditioned medium of COS cells transfected with plasmids Δ188–227, Δ188–227/L 108S, and GAG 104. Binding levels are compared to that of OM secreted from COS cells (SPOM) (Linsley, et al., 1990, Mol. Cell. Biol. 10:1882–1890.

Figure 7:
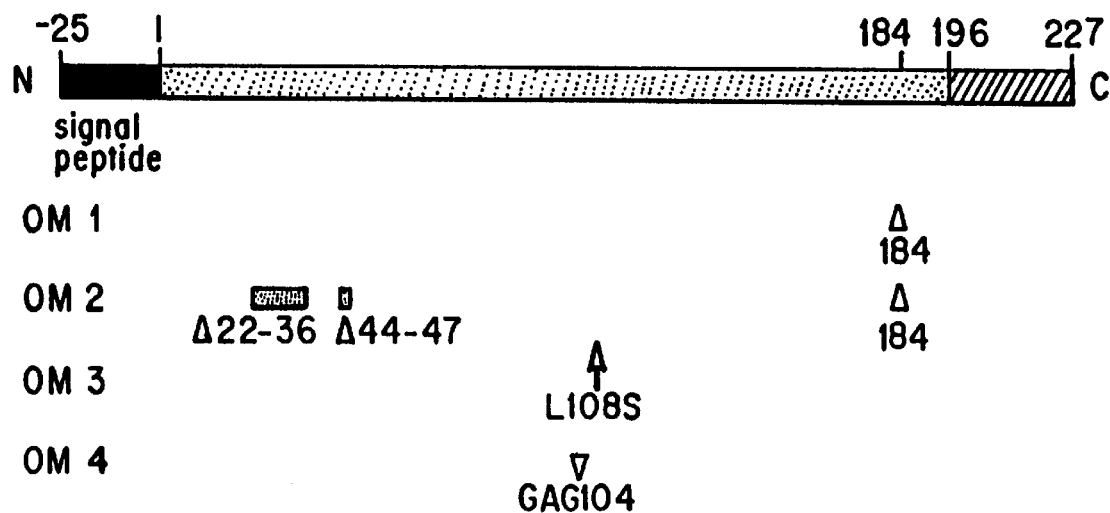

FIG. 7. Schematic diagram of mutations of Oncostatin M which affect the binding of a series of monoclonal antibodies directed against Oncostatin M. The leader sequence of OM is located from residues −25 to −1. The unprocessed molecule secreted from COS cells is 227aa in length, and is cleaved to a mature 196aa protein (Linsley, et al., 1990, Mol. Cell. Biol. 10:1882–1890). The deletion of C-terminal amino acids internal to and including 184 (Δ) destroys the binding of both OM1 and OM2. Additionally, OM2 binding is abrogated by deletions of residues 22–36 or 44–47. The epitope of antibody OM3 is mapped to a site containing residue 108 (arrow) since a change from leucine to serine at this residue destroys binding of this mAb. The insertion of the glycine-alanine-glycine tripeptide at residue 104 (▽) abolishes OM4 binding.

5. DETAILED DESCRIPTION OF THE INVENTION

The present invention relates to monoclonal antibodies specific for Oncostatin M, a novel cytokine which exhibits pleiotropic effects on a wide variety of normal and transformed cells. Monoclonal antibodies which bind Oncostatin M, inhibit Oncostatin M receptor binding, and/or inhibit Oncostatin M bioactivity are described.

The monoclonal antibodies described herein can be used to map epitopes of Oncostatin M and to define structure-function relationships of its domains. Such antibodies may be used in diagnostic assays, for example, to detect the presence of Oncostatin M, or mutant forms of Oncostatin M. Alternatively, the monoclonal antibodies may be employed to modulate Oncostatin M biological activities in an in vivo or in vitro system. The invention is described in detail in the subsections below.

5.1. Characteristics of Monoclonal Antibodies Defined by their Specificity for Oncostatin M Monoclonal antibodies which define various epitopes of native and/or denatured forms of Oncostatin M are described. The monoclonal antibodies are further classified by their ability to block Oncostatin M biological activity and/or binding to cell surface receptors. Any monoclonal antibody, including chimeric antibodies which competitively inhibit the immunospecific binding of the monoclonal antibodies described herein to their Oncostatin M epitopes are within the scope of the invention.

5.1.1. Oncostatin M Antigen Recognition

Oncostatin M, originally identified for its inhibitory effects on human tumor cell lines, was first isolated from phorbol 12-myristate 13-acetate (PMA)-induced human histiocytic lymphoma cells (Zarling et al., 1986, Proc. Natl. Acad. Sci. USA 83:9739–9743) and from activated T lymphocytes (Brown et al., 1987, J. Immunol. 139:2977–2983). The molecule is a heat and acid stable protein comprised of a single polypeptide chain of $M_r$=28,000. Like other naturally occurring growth regulators, Oncostatin M exhibits a variety of biological activities. Growth inhibition is observed with some, but not all, human tumor cell lines. In contrast, the growth of some normal fibroblasts, such as human foreskin fibroblasts or WI-38 cells, is stimulated by exposure to Oncostatin M (Zarling et al., 1986, Proc. Natl. Acad. Sci. USA 83:9739–9743). The gene for Oncostatin M has been cloned and sequenced, and an active form of recombinant Oncostatin M has recently been expressed in mammalian cells (copending application Ser. No. 144,574 filed Jan. 15, 1988, which is incorporated herein by reference in its entirety). The mature form, after cleavage of the signal peptide, is a glycoprotein containing 227 amino acids, five of which are cysteine residues. The protein has an extremely hydrophilic carboxy terminal domain. Although oncostatin M is not structurally related to other known cytokines, its mRNA contains an AU-rich region at its 3' untranslated end. This region in the Oncostatin M message is homologous to that of many cytokines, lymphokines and other growth-regulatory molecules, suggesting a common mode of regulating gene expression. A cellular receptor for Oncostatin M has been found on a variety of mammalian cells. The major Oncostatin M receptor molecule is a specific protein of Mr=150,000–160,000 (Linsley et al., 1989, J. Biol. Chem. 264:4282–4289).

Oncostatin M may be obtained by techniques well known in the art from a variety of cell sources which synthesize bioactive Oncostatin M including, for example, cells which naturally produce Oncostatin M and cells transfected with recombinant DNA molecules capable of directing the synthesis and/or secretion of Oncostatin M. Alternatively, Oncostatin M may be synthesized by chemical synthetic methods including but not limited to solid phase peptide synthesis. Methods for the production of Oncostatin M are described in copending application Ser. No. 144,574 filed Jan. 15, 1988, a continuation-in-part of application Ser. No. 046,846 filed May 4, 1987, a continuation-in-part of application Ser. No. 935,283 filed Nov. 26, 1986, a continuation-in-part of application Ser. No. 811,235 filed Dec. 20, 1985, each of which is incorporated by reference herein in its entirety.

Monoclonal antibodies with an affinity for Oncostatin M may be selected by assaying their capacity for binding Oncostatin M using any of a number of immunological assays, including but not limited to, enzyme linked immunosorbant assay (ELISA), immunoprecipitation, Western blot analysis, radio-immunometric assays, competitive and non-competitive immunoassays. For example, the solid phase micro-enzyme assay (MicroEIA) described in Section 6.1.2., infra, may be readily used. Briefly, antibodies found in the supernatant of hybrids are assessed by their ability to bind to Oncostatin M coated to a solid surface in wells. Following the addition of the supernatant, peroxidase-conjugated F(ab)$_2$ goat anti-mouse Ig is added to the well. After washing away any unbound material, the bound enzyme is revealed by addition of a substrate which undergoes a color change. The color change, infra, indirectly indicates a monoclonal antibody Oncostatin M complex formed in the well.

5.1.2. Inhibition of Oncostatin M Activity

Antibodies which inhibit the biological activity of Oncostatin M may find particular use in therapeutic applications. Such antibodies can be identified using the Growth Inhibition Assay (GIA) as described in Section 6.1.4. and, infra. Briefly, GIA provides a test system to assess the ability of an antibody to neutralize the inhibitory effects of Oncostatin M on the growth and proliferation of target cells.

5.1.3. Inhibition of Binding to Oncostatin M Receptor

Cell surface receptors generally have a high affinity for their ligand, the binding of the ligand to the specific cell surface receptor initiates the control of various cellular events. Binding of Oncostatin M to a membrane receptor has been demonstrated using the radioreceptor assay described in Section 6.1.5. and infra, and in Copending Application Ser. No. 144,574, filed Jan. 15, 1988. The human tumor cells tested included A375 (melanoma); A875 (melanoma); Me1109 (melanoma); T24 (bladder carcinoma); A549 (lung adenocarcinoma); H1477 (melanoma); Me108 (melanoma); and MCF (breast). Binding of $^{125}$I-Oncostatin M was specific and saturable, and was not inhibited by other known polypeptide growth regulators. Scatchard analysis of binding data obtained with different cell lines revealed that $^{125}$I-Oncostatin M bound to $1-2\times10^4$ binding sites per cell with a $K_d$ of approximately $10^{-9}$M. The monoclonal antibodies produced by the hybrids were tested for their ability to block the binding of Oncostatin M to its cell surface receptor using the radioreceptor assay as described in Section 6.1.5. and, infra.

5.2. Methods for Preparing Monoclonal Antibodies to Oncostatin M

The anti-Oncostatin M antibodies of the invention can be prepared using any of a variety of techniques in which Oncostatin M is used as an immunogen injected into a mammalian host, e.g. mouse, cow, goat, sheep, rabbit, etc., particularly with an adjuvant, e.g. complete Freunds adjuvant, aluminum hydroxide gel, or the like. The host may then be bled and the blood employed-for isolation of polyclonal antibodies. Alternatively, the peripheral blood lymphocytes, splenic lymphocytes (B-cells), or lymph node lymphocytes may be employed for fusion with an appropriate myeloma cell to immortalize the chromosomes for monoclonal expression of antibodies specific for Oncostatin M.

While the invention is described by way of examples using mouse monoclonal antibodies, the invention is not so limited and encompasses the use of, for example, human antibodies. Such antibodies can be obtained by using human hybridomas (Cote et al., 1983, Proc. Natl. Acad. Sci. U.S.A., 80:2026–2030) or by transforming human B cells with EBV virus in vitro (Cole et al., 1985, in, Monoclonal Antibodies and Cancer Therapy, Alan R. Liss, pp. 77–96). Techniques recently developed for the production of "chimeric antibodies"0 may be employed (Morrison et al., 1984, Proc. Natl. Acad. Sci. U.S.A., 81:6851–6855; Neuberger et al., 1984, Nature 312:604–608; Takeda et al., 1985, Nature 314:452–454), which techniques involve splicing the genes from a mouse antibody molecule of appropriate antigen specificity together with genes from a human antibody molecule of appropriate biological activity.

A technique recently described can be used to generate a repertoire of monoclonal antibodies that define Oncostatin M (see Sastry et al., 1989, Proc. Natl. Acad. Sci. 86:5728–5732; and Huse et al., 1989, Science 246:1275–1281). Accordingly, a cDNA library of Fab fragments derived from splenic DNA of animals primed with Oncostatin M can be generated in bacterial host cells.

The monoclonal antibodies of the invention can be modified by treatment with appropriate proteases, e.g., pepsin, papain, and the like, to generate Fab, F(ab')$_2$ or F$_V$ fragments that immunospecifically bind to Oncostatin M.

Additionally, the whole antibody molecule or its Fab, F(ab')$_2$ or F$_V$ fragment may be conjugated to any of a variety of compounds including, but not limited to, signal generating compounds such as a fluorescer, radiolabel, a chromophore, an enzyme, a chemoluminescent or bioluminescent molecule, etc. Alternatively, the whole antibody or its Fab, F(ab')$_2$ or F$_V$ fragment may be conjugated to a growth factor which may enhance or inhibit the biological activity of Oncostatin M; or to toxins so that cells which express Oncostatin M precursors on their surface would be selectively killed. Methods which can be used for conjugating labels, proteins, toxins etc. to antibodies and antibody fragments are well known in the art. See, for examples U.S. Pat. Nos. 4,220,450; 4,235,869; 3,935,074; and 3,996,345.

5.3. Uses of Monoclonal Antibodies to Oncostatin M

The antibodies of the invention may be advantageously used to detect native or denatured forms of natural or recombinant Oncostatin M; to detect the presence of Oncostatin M in serum samples where it may occur in a free form or associated with its binding protein. Alternatively, the antibodies of the invention may be used in vivo to inhibit the biological effects of Oncostatin M. Either polyclonal or monoclonal antibodies may be used for the detection of Oncostatin M in a sample, such as cells or physiological fluid, e.g., blood. Detection of Oncostatin M in a body fluid may also be used as an indication of the presence of a tumor cell. In this regard, anti-Oncostatin M antibodies may be useful in the diagnosis and/or prognosis of cancer and/or other cell growth-related disease. The antibodies may also be used in affinity chromatography for isolating and purifying Oncostatin M from natural or synthetic sources. The antibodies will also find use in controlling the amount of Oncostatin M associated with cells in culture or in vivo, whereby growth of the cells may be modified by the formation of specific antibody:Oncostatin M complex resulting- in competitive inhibition of Oncostatin M:Oncostatin M receptor binding. Thus, the antibodies of the invention may be useful as therapeutic agents in the treatment of cell growth disorders in which the growth stimulating activity of Oncostatin M is a factor.

5.3.1. Generation of Anti-Idiotypes that Mimic the Effects of Oncostatin M

The monoclonal antibodies of the invention can also be used to generate anti-idiotypic antibodies that mimic the biological effects of Oncostatin M. Anti-idiotypic antibodies or anti-idiotypes are antibodies directed against the antigen-combining region or variable region (called the idiotype) of another antibody molecule. In theory, based on Jerne's network model of idiotypic relationships (Jerne, N. K., 1974 Ann. Immunol. (Paris) 125:373; Jerne, N. K. et al., 1982, EMBO (234), immunization with an antibody molecule expressing a paratope (antigen-combining site) for a given antigen should produce a group of anti-idiotypic antibodies, some of which share with the antigen a complementary structure to the paratope. Immunization with monoclonal antibodies that inhibit binding of Oncostatin M to its receptor should in turn produce anti-idiotypes that mimic Oncostatin M and bind to the Oncostatin M receptor. Thus it is in the present scope of the invention that these anti-idiotypes can be produced by the monoclonal antibodies directed against Oncostatin M which will mimic the effects of Oncostatin M in vivo and in vitro. Likewise, anti-idiotypic antibodies that bind to Oncostatin M are intended to be included in the definition of monoclonal antibodies that define Oncostatin M as used herein.

5.3.2. Oncostatin M Epitope Mapping

Structural analysis of the growth regulator, Oncostatin M, is an important prelude to determining the biological role this novel cytokine plays in homeostasis or pathological states. In the examples described infra, we have analyzed a series of monoclonal antibodies (OM1 through OM8) produced against recombinant Oncostatin M to determine their structural binding requirements and epitope localization. These antibodies detect either linear (OM3 and OM4) or folded epitopes (OM1 and OM2). The linear epitopes detected by OM3 and OM4 are situated in close proximity. It is intriguing that OM3, whose epitope includes residue 108, reacts with both folded and denatured Oncostatin M, while MAb OM4, whose epitope is disrupted by insertion of a tripeptide at amino acid residue 104, binds only denatured Oncostatin M.

Monoclonal antibody, OM2 abrogated the functional effects of Oncostatin M in a growth inhibition assay. The data presented infra indicate that antibody OM2 antagonizes the effects of OM by preventing OM from binding to its receptor. Through serological analysis, we were able to identify that certain amino acid insertion, deletion, or substitution mutations affect the binding of the neutralizing antibody. The results of these experiments correlate very closely with those obtained by analysis of the GIA and RRA activity of these mutant molecules, and suggest that the neutralizing antibody binding site lies within the tertiary structure of the OM molecule which requires proper folding for biological activity.

The disruption of both receptor and OM2 binding in mutants having deletions or changes in non-contiguous (C terminal, Δ22–36, Δ44–47) amino acid residues strengthen the interpretation that the functionally important region(s) of Oncostatin M is highly dependent on proper tertiary structure. These data additionally suggest that regions in both the N-terminus and C-terminus of the mature molecule are essential for the functional activity of Oncostatin M, whether directly by forming the receptor binding site or indirectly by stabilizing the tertiary structure necessary for activity.

Similar observations have been made for interleukin-6, which shares some functional properties with Oncostatin M including in vitro growth inhibition of certain tumor cell lines and induction of plasminogen activator activity (Brown, et al., 1990, in Molecular Biology of the Cardiovascular System, Elsevier, Amsterdam, pp. 195–206). Concomitant deletion of both the N-terminal amino acids past residue,31 and the first five carboxy terminal amino acids of IL-6 markedly reduces activity, while deletion of the sixteen C-terminal residues completely abolishes functional activity. A series-of neutralizing antibodies to IL-6 appear to recognize epitopes formed by amino and carboxy terminal amino acids, and an alpha helical structure likewise has been proposed for the seven C-terminal amino acids of IL-6 (Brakenhoff, et al., 1990, J. Immunol. 145:561–568. In contrast to the results presented for Oncostatin M, intramolecular disulfide bonds do not seem to be essential for IL-6 functional activity (Jambou, et al., 1988, Proc. Natl. Acad. Sci. USA 85:9426–9430). Neutralizing monoclonal antibodies have been produced to α interferon (Cebrian, et al., 1987, J. Immunol. 138:484–490) and β interferon (Redlich & Grossberg, 1989, J. Immunol. 143:1887–1893) and, as with Oncostatin M, disulfide linkage is required for functionality. Epitope mapping on mutant interferon molecules has not been published. The compilation of structure-function analysis for these and other cytokines should aid in delineating how similar tertiary structural and functional features of these molecules can be accommodated by dissimilar primary structures. A schematic model of the functionally important regions of the Oncostatin M molecule determined so far with OM2, and with the mapping of the OM3 and OM4 epitopes is presented in FIG. 7.

The internal deletion mutant data reveal that, although the neutralizing antibody binding site is lost, the epitope detected by the non-neutralizing antibody, OM1, remains intact. Similar results have been obtained by alanine-scanning mutagenesis of the human growth hormone, in which numerous mutations can affect receptor binding without affecting binding of those monoclonal antibodies directed against epitopes other than the receptor binding region (Cunningham & Wells, 1989, Science 244:1081–1085. These data indicate that local disruptions of the receptor binding site can occur without causing massive disruption of the tertiary structure of Oncostatin M. The mapping of the OM1 epitope has not been possible based on the mutants generated so far. It may be that the OM1 epitope depends on tertiary structure stabilized by the folding of the C-terminus.

Several complementary approaches to examining structure-function relationships of Oncostatin M have been described here and elsewhere. Because the antibody OM2 appears to exert its neutralizing activity by blocking Oncostatin M binding to its receptor, the potential exists for generating an anti-idiotypic antibody directed against the internal image of the neutralizing antibody which could recognize the oncostatin M receptor. This approach has been applied successfully to the generation of antibodies directed against a number of different receptors, such as the insulin receptor (Sege & Peterson, 1978, Proc. Natl. Acad. Sci. USA 75:2443–2446), and the β-adrenergic receptor (Schreiber, et al., 1980, Proc. Natl. Acad. Sci. USA 77:7385–7389, Homey, et al., 1982, J. Clin. Invest. 69:1147–1154), among others (Gaulton & Green, 1986, Ann. R Immunol. 4:253–280, Vaux, et al., 1990, Nature 345:495–502. Localization of the epitopes detected by the monoclonal antibodies described here provides us with important reagents with which we may now examine the biological function and tissue distribution of Oncostatin M.

6. EXAMPLE

Production of Monoclonal Antibodies to Oncostatin M

The subsections below describe the production and characterization of monoclonal antibodies to Oncostatin M, including monoclonal antibodies that neutralize Oncostatin M growth inhibitory activity.

6.1. Materials and Methods

6.1.1. Immunization and Fusion

The hybridomas were produced by immunization of 4 Balb/c mice with either 5 µg or 10 µg of recombinant Oncostatin M expressed by CHO cells transfected with the plasmid pBOM (Linsley, et al., 1989, J. Biol. Chem. 264:4282–4289) and purified as described (Zarling, et al., 1986, Proc. Natl. Acad. Sci. USA 83:9739–9743). The transfected CHO cells secrete Oncostatin M as a mature molecule of 196 amino acids which is processed from a 227 residue precursor molecule (Linsley, et al., 1990, Mol. Cell. Biol. 10:1882–1890).

Briefly, the Oncostatin M was resuspended in PBS, emulsified in an equal volume of Complete Freund's Adjuvant, and 25 µg of the emulsion was injected into one hind footpad intradermally. Two weeks later, the same immunization protocol in the same hind footpad was followed, with concentrations of Oncostatin-M identical to that for the first immunization. Two weeks after the second immunization, the mice were injected in the same hind footpad with a third preparation of Oncostatin-M, this time emulsified in Incomplete Freund's Adjuvant. Three days after the final immunization, the popliteal lymph node was removed, and the lymph node cells were fused with murine myeloma 653/AG8 cells at a 1:1 lymph node cell to myeloma cell ratio, using 40% polyethylene glycol as a fusion agent. Fusion products at a concentration of $5 \times 10^4$ cells/well were plated into 96-well plates containing hypoxanthine-aminopterin-thymidine as selection agent, in Iscoves Modification of Dulbecco's Modified Eagle's Medium (IDMEM) supplemented with 10% fetal bovine serum, sodium pyruvate, and L-glutamine. After one week, original medium was replaced with fresh medium containing selection agent. Hybrids were screened by a solid-phase Micro Enzyme-linked Assay (Micro EIA), when the hybrids were visible macroscopically, as described in Section 6.1.2, infra.

6.1.2. Enzyme-Linked Immunoassays

The following Micro EIA was used to characterize the specificity of the antibodies to Oncostatin M produced by the hybridomas. Hybrid supernatants were screened for activity using a solid-phase EIA adapted for use in Microtest plates (Robbins Scientific, San Francisco). Concentrations of purified Oncostatin-M ranging from 2 to 4 µg/ml were plated in 5 µl volumes in each well, and allowed to air-dry overnight. After a one hour block with 5% nonfat dried milk in PBS and 0.1% sodium azide, the hybrid supernatants were added in 1 µl volumes, and incubated at room temperature for 1 hour. The plates were washed six times by immersion in PBS. Peroxidase-conjugated $F(ab')_2$ goat anti-mouse IgG (Pel-Freez, Rogers AK) in PBS+2% BSA at a concentration of 1:1500 was added in 5 µl volumes to each well. After a 1 hour incubation, the plates were washed six times as previously described; 10 µl of substrate (ABTS) was added, and plates were read at OD=660 nm after 20 minutes. Positive wells were determined on the basis of signal above background relative to the signal of a previously generated rabbit antiserum against Oncostatin-M. Positive hybrids were cloned in soft agar.

A double determinant EIA (DDEIA) was employed to evaluate the ability of monoclonal antibodies whose epitopes have tertiary structure to bind to a series of mutant Oncostatin M molecules. These mutants contained insertions, deletions, or substitutions in amino acid residues at various sites in the molecule. A direct EIA employing mAb OM3 was utilized to assess concentrations of the mutant molecules in the supernatants prior to their analysis in the DDEIA. For the DDEIA, 100 µl of Protein G (Pharmacia) affinity-purified monoclonal antibody OM3 at a concentration of 10 µg/ml in 0.05M carbonate buffer, pH 9.6, was added to 96-well flat-bottomed plates, and incubated overnight at 4° C. The antibody was removed, and after one hour of blocking with PBS, 1% BSA, 0.05% Tween 20, either purified Oncostatin M at defined concentrations or serial dilutions of supernatants from COS cells transfected with plasmids encoding mutant forms of OM was added. The plates were incubated for 2 hrs at 37° C., washed five times with PBS, and incubated again for 1 hr at 37° C. with 100 µl of a 200 ng/ml concentration of biotinylated monoclonal antibody (OM1 or OM2). After a 1 hr incubation at 37° C., plates were washed 5 times; 100 µl of a 1:10,000 dilution of HRP-conjugated streptavidin (Vector) were added and the plates incubated for 30 minutes at 37° C. After washing, the reaction was developed with 3, 3', 5, 5' tetramethylbenzidine (TMB), stopped with 1N sulfuric acid, and A450 was read.

6.1.3. Immunoprecipitation

CHO cells transfected with the Oncostatin-M-encoding cDNA (Linsley, et al., 1989, J. Biol. Chem. 264:4282–4289) were incubated for 4–8 hr with 200 µCi each of $^{35}S$ methionine and $^{35}S$ cysteine in a volume of 4 ml in a 60×15 cm petri dish. Supernatants were collected and filtered; 10 mM (PMSF) and 100 mM TLCK were added to inhibit proteases. For immunoprecipitations, 100–200 µl of labelled supernatant were incubated with 200 µl of spent supernatant from the monoclonal antibody-secreting hybrids overnight at 4° C. with rotating. Antigen-antibody complexes were isolated by incubation with a monoclonal rat anti-mouse k light chain monoclonal antibody covalently coupled to Reactigel beads (Pierce Chemicals). After washing, the antigen-antibody complexes were eluted by boiling in sample buffer containing 1% SDS and 5% 2-mercaptoethanol. The eluted material was electrophoresed in 15% SDS-PAGE. Gels were fluorographed with Amplify (Amersham), dried, and autoradiographed with Kodak X-AR5 X-ray film.

6.1.4. Growth Inhibitory Assay

The antibodies were tested to determine whether any could neutralize the inhibitory effects of Oncostatin-M in a Growth Inhibitory Assay (GIA). The GIA employs A375 melanoma cells ($4 \times 10^3$ cells/50 μl) as indicator cells. A375 cells are subcultered for four hours on flat-bottomed 96-well tissue culture plates (Costar 3595, Cambridge, Mass.) in growth medium comprising Dulbecco's modified Eagle's medium (DMEM), supplemented with 10% heat-inactivated fetal bovine serum, and penicillin/streptomycin. Oncostatin M is diluted in growth medium and assayed for growth inhibition in triplicate by adding 50 $\mu^1$ of the diluted sample per well. The cells are then incubated for 72 hours at 37° C. At the end of this incubation period, each well is treated for 24 hours with 100 μl of growth medium containing [$^{125}$I]iodo-2'-deoxyuridine (0.05 μCi/well (Amersham, Arlington Heights, Ill.). The monolayers are washed with phosphate-buffered saline (PBS), fixed in 95% methanol and air-dried. The [$^{125}$I]-iododeoxyuridine incorporated by the cells is solubilized with 200 μl of 1N sodium hydroxide and the amount of cell growth measured by the amount of [$^{125}$I]iododeoxyuridine incorporated into the DNA of actively growing cells. One unit of activity is defined as the amount of the Oncostatin M required to give 50% inhibition of growth of A375 cells relative to untreated cells.

6.1.5. Oncostatin M Radioreceptor Assay

Antibodies were tested in a radioreceptor assay for the ability to inhibit the binding of $^{125}$I-labeled Oncostatin-M to cell surface receptors for Oncostatin M on the human carcinoma cell line H2981. H2981 cells are plated in 48-well plates at a density of $2 \times 10^5$ cells/well and maintained at 37° C. for 16–24 hours before initiation of the assay. Cell monolayers are then washed once with Binding Buffer exhibited activity in fractions of molecular weights greater than 200 kilodaltons, suggesting that the Oncostatin-M in serum is generally associated with a binding factor of greater than 200 kd, and is inactive in this state. The various serum fractions were examined by Western blotting. Reaction of the Oncostatin-M-specific monoclonal antibodies with proteins found in the high molecular weight fractions corresponding to the molecular weight of Oncostatin-M, confirmed the presence of Oncostatin-M in these fractions. The Oncostatin-M found in serum has been purified, and N-terminal amino acid sequencing indicates that it is identical to the native and recombinant Oncostatin-M previously obtained.

6.2. Results

6.2.1. Selection of Monoclonal Antibodies with Specificity for Oncostatin M Two series of fusions were performed, consisting of four fusions in each series, with one lymph node from each mouse used per fusion. From the first series, four hybrids were examined more extensively. From the second, more successful series of fusions (in terms of numbers of positive hybrids identified in the MicroEIA), at least 20 other anti-Oncostatin-M monoclonal antibodies were identified. From this number, the following hybrids were selected for further study based on relative signal in the EIA and ability to immunoprecipitate either native or denatured metabolically labelled Oncostatin-M: OM2, OM7, OM3, and OM8. Based on the immunoprecipitation data described in Section 6.2.2 infra, the hybrids were grouped into one of three categories based on their reactivities with either native Oncostatin M, denatured or both (Table I). Five of these monoclonal antibodies were then tested to determine whether any of them could neutralize the (Linsley et al., 1986, Biochemistry 25:2978–2986). To measure total binding, $^{125}$I-Oncostatin M was added at concentrations ranging from 0.5–100 ng/ml. To measure non-specific binding, unlabeled Oncostatin M is added simultaneously with the $^{125}$I-Oncostatin M to replicate plates at a concentration 20 to 100-fold higher than the concentration of $^{125}$I-Oncostatin M. Binding is allowed to proceed for 2–5 hours at 23° C., then the monolayers are washed four times with Binding Buffer. Cell-bound radioactivity is solubilized with 1N NaOH and counted in a gamma counter. Specific binding is calculated by subtracting the non-specific binding from total binding. The dissociation constant ($K_d$) and binding capacity was determined by Scatchard analysis (Scatchard, 1949, Ann. N.Y. Acad. Sci. 51:660).

6.1.6. Oncostatin M Mutants

Anti-Oncostatin M monoclonal antibodies were tested against a series of recombinant Oncostatin M mutants, having insertions, deletions or substitutions, generated at the DNA level. The antibodies were tested as spent supernatants in an EIA on media from COS cells which were transfected transiently with the various parental and mutant constructs.

6.1.7. Detection of Oncostatin M in Serum with Monoclonal Antibodies

The presence of Oncostatin-M in serum was detected as follows: Human serum samples were first applied to an S-300 sizing column to separate serum proteins by molecular weight. Fractions collected from the S-300 column were examined for GIA activity, both before and after acidification of the serum samples. Before acidification, most serum samples exhibited no GIA activity in the void volume fractions. However, serum fractions which were acidified, then reneutralized before adding to the GIA inhibitory effects of Oncostatin-M in the Growth Inhibitory Assay, the results are described in Section 6.2.3, infra.

TABLE I

Anti-Oncostatin M Monoclonal Antibodies

| Antibody | Isotype | Corresponding Lane in FIG. 1 | Reactive Form of OM[a] | Reactivity in Dot Blotting | Neutralizing Activity[b] |
|---|---|---|---|---|---|
| OM1 | IgG2a | 2 | Native | − | No |
| OM5 | IgG2a | 3 | Denatured | + | No |
| OM6 | IgG2a | 4 | Denatured | + | No |
| OM4 | IgG2a | 5 | Denatured | + | No |
| OM2 | IgG1 | 6 | Native | − | Yes |
| OM7 | IgG1 | 7 | Native | − | Yes |
| OM3 | IgG2b | 8 | Native or | ++ | No |

TABLE I-continued

Anti-Oncostatin M Monoclonal Antibodies

| Antibody | Isotype | Corresponding Lane in FIG. 1 | Reactive Form of OM[a] | Reactivity in Dot Blotting | Neutralizing Activity[b] |
|---|---|---|---|---|---|
| OM8 | IgG2b | 9 | Denatured Native or Denatured | ++ | N.D. |

[a]As determined by immunoprecipitation
[b]AS determined by GIA
ND = Not Determined

6.2.2. Monoclonal Antibodies Immunoprecipitate with Oncostatin M

Results of immunoprecipitation data identified three monoclonal antibodies (OM1, OM2 and OM7) reacting only with $^{35}$S-methionine-labelled Oncostatin-M in the form in which it was secreted from the CHO transfectant (group 1) (lanes 2,6,7; FIG. 1; see Table I for identification of antibodies). Three additional monoclonal antibodies (OM4, OM5 and OM6) reacted only with $^{35}$S-methionine-labelled Oncostatin-M which was first reduced and denatured by treating with SDS and reducing agents, then boiled at 100 degrees C, but not with native Oncostatin-M (group 2, lanes 3,4,5). Two additional monclonal antibodies (OM3 and OM8) reacted with biosynthetically labelled Oncostatin-M whether it was native or denatured (group 3, lanes 8,9).

Figure 2A:
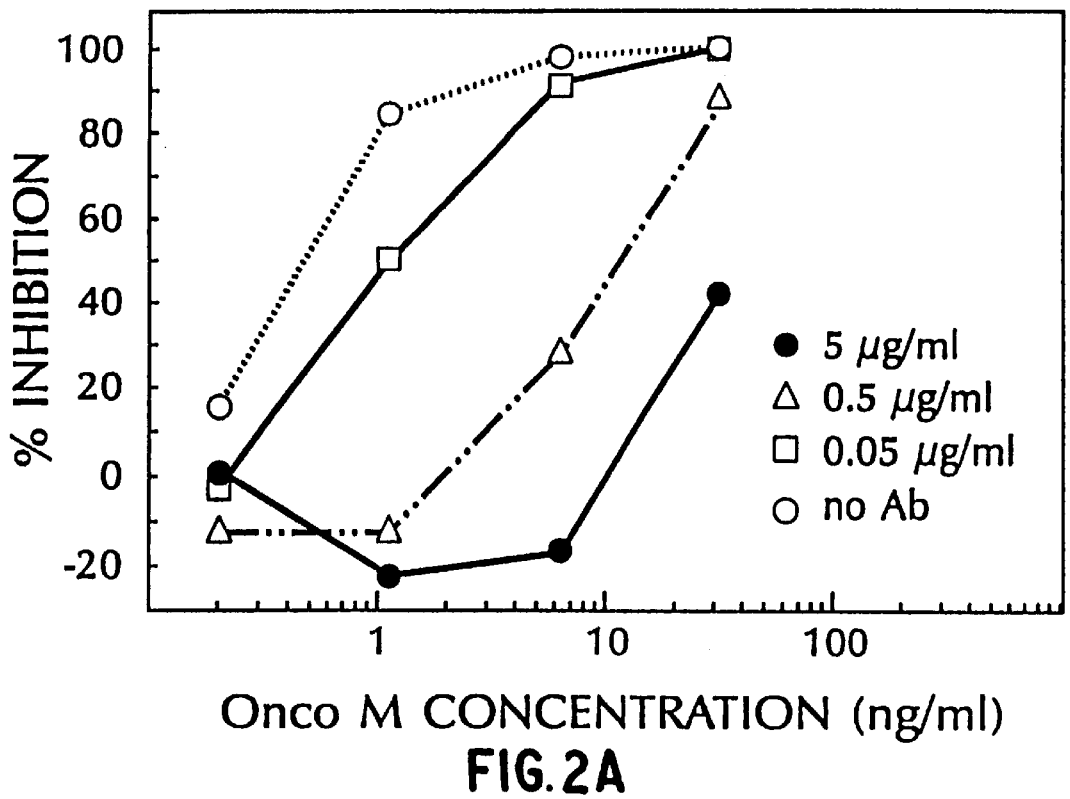
Figure 2B:
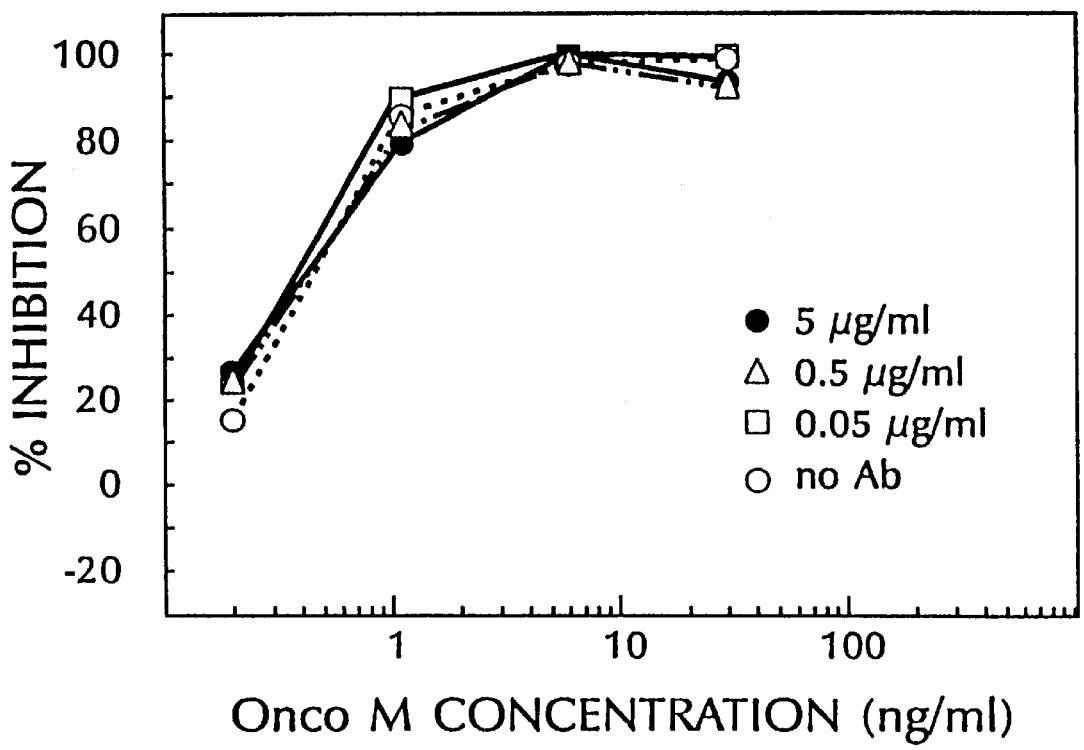

6.2.3. Monoclonal Antibodies that Neutralize Oncostatin M in the Growth Inhibition Assay Purified antibody from the hybrid OM2 neutralized the effects of Oncostatin-M in a concentration-dependent fashion (FIG. 2A). Antibody OM1, which is directed against native Oncostatin-M, showed no blocking of growth inhibitory effects of Oncostatin-M (FIG. 2B). None of the antibodies detecting a denatured determinant was capable of neutralizing Oncostatin-M as measured by GIA. The neutralizing antibody OM2 was further tested for its ability to inhibit Oncostatin-M receptor binding, as described in Section 6.2.4, infra.

6.2.4. Monoclonal Antibodies that Inhibit Binding of Oncostatin M in the Radioreceptor Assay The OM2 antibody was capable of inhibiting Oncostatin-M receptor binding in a concentration dependent fashion, in contrast to either the OM1 antibody, directed against a native but non-neutralizing site, or a third antibody, OM4, directed against an epitope on denatured Oncostatin-M (FIG. 3).

6.3. Analysis of Functional Sites and Epitope Mapping of Oncostatin M

The subsections below describe the characterization of monoclonal antibodies generated against recombinant OM purified from supernatants of transfected CHO cells (Linsley et al., 1989, J. Biol. Chem. 264:4282–4289). Through serological analysis of products secreted by COS cells transfected with plasmids encoding a series of mutant forms of OM, we have mapped some of the epitopes detected by the monoclonal antibodies and determined some of the tertiary structural requirements for both antibody binding and functional activity of the OM molecule.

Of the two antibodies which detect folded epitopes, OM2, but not OM1, was identified as a neutralizing antibody based on its ability to abrogate OM activity in the growth inhibition assay (GIA) and to inhibit OM binding in the radioreceptor assay (RRA). Serological analysis of the mutant OM molecules demonstrated that the binding site of OM2 is affected by noncontiguous regions of OM, and that the presence of one of the two disulfide bonds (C49–C167) is essential for neutralizing antibody binding. In addition, certain mutations abrogate OM2 binding without causing global misfolding of the OM molecule.

These data indicate that the epitope defined by OM2 is spatially related to the binding site of OM, while those detected by OM1, OM3 and OM4 are distinct. The antibodies described here represent immunological probes for detecting OM in tissues and fluids of interest and will be useful in defining the physiological function and distribution of OM.

6.3.1. Mapping of OM Epitopes by EIA on Oncostatin M Mutants

The growth regulator Oncostatin M (OM) is a novel cytokine which exhibits pleiotropic effects on a wide variety-of normal and transformed cell lines. To determine some of the physiological functions of OM we have developed and characterized a series of monoclonal antibodies (OM1, OM2, OM3, and OM4) to the recombinant molecule as described in the subsections below.

Antibodies OM1 and OM2 bound native, but not denatured OM, suggesting they recognized epitopes with tertiary structural conformation. A third antibody, OM3, bound native or denatured ON, and antibody OM4 bound only denatured OM. Epitopes for these monoclonal antibodies (mAb) were localized by measuring antibody binding to a panel of mutant forms of OM. The OM3 binding site contains residue 108, while that for OM4 is disrupted by amino acid insertions at position 104.

In order to map the epitopes detected by these antibodies, we tested their binding to OM in serum-free conditioned medium from COS cells transfected with a series of plasmids encoding OM mutations in amino acid residues at various sites in the molecule. Antibodies OM3 and OM4, which detect linear epitopes, were examined in direct EIA for binding to a series of mutant OM proteins from which C-terminal amino acids were deleted, in sequential fashion by means of stop codon insertions (FIG. 6). Mutant Δ188–227 was bound by OM3, while Δ188–227/L108S, with an additional change from leucine to serine at residue 108, was not bound. Antibody OM4 was mapped to a site which was disrupted by the insertion of a glycine-alanine-glycine sequence at position 104 (FIG. 6). Antibodies OM5 and OM6, which also reacted predominantly with denatured OM, did not react with the same epitope as OM4, since they reacted with the GAG104 mutant, which is not bound by OM4. None of the series of OM mutants generated thus far was informative in the epitope mapping of these mutants. Antibody OM7 is probably identical to antibody OM2, the neutralizing antibody, since it has the same Ig isotype and OM mutant binding patterns as OM2, while antibodies OM8 and OM3 are probably identical for the same reason.

6.3.2. Serological Analysis of OM1 and OM2 Epitopes

In order to analyze the OM structural requirements for binding of antibody OM1 and OM2, both of which reacted only with folded forms of OM, we developed a double determinant EIA. The assay employed antibody OM3, which bound either native or denatured OM, to capture the OM from the COS transfectant mutant supernatants. The concentrations of OM (from the mutant molecules) bound by either biotinylated OM1 or OM2 were compared to a standard curve of purified native OM bound by the respective antibodies.

Results are presented in Table II as the concentration of OM mutant molecules bound by these antibodies, in ng/ml, compared to their binding of purified OM. Because this assay was saturated at the concentrations of OM present in undiluted supernatants of the mutant transfectants, serial dilutions were required to detect OM in the linear portion of the DDEIA. In all cases where the extrapolated values of detected OM were greater than 200 ng/ml, the absorbance values of the dilution series for the different mutant on molecules had the same slope, indicating that the biotinylated antibodies bound such mutant molecules with the same relative affinity.

TABLE II

RELATIVE ABILITIES OF MONOCLONAL ANTIBODIES OM1 AND OM2 TO BIND TO VARIANT FORMS OF ONCOSTATIN M IN DOUBLE DETERMINANT EIA*

| Plasmid | Change from Parental Form | Relative Reactivity (ng/ml) | |
|---|---|---|---|
| | | OM1 | OM2 |
| pSPOM | parental form | 1690 | 1780 |
| Δ186-227 | deletion of 42 residues from C terminus | >2000 | >2000 |
| Δ185-227 | deletion of 43 residues from C terminus | 1900 | 840 |
| Δ184-227 | deletion of 44 residues from C terminus | 15 | 35 |
| Δ172-227 | deletion of 55 residues from C terminus | 0 | 100 |
| F184G | change of phenylalanine to glycine | >2000 | 1650 |
| F176G | change of phenylalanine to glycine | 250 | 50 |
| F169G | change of phenylalanine to glycine | >2000 | >2000 |
| H178G | change of histidine to glycine | >2000 | >2000 |
| H174G | change of histidine to glycine | >2000 | 2000 |
| C6S/C167S | change from cysteines at 6 and 167 to serine | 0 | 0 |
| C6S | change from cysteine at 6 to serine | 1750 | >2000 |
| Δ44-47 | deletion of 3 internal residues | >2000 | 50 |
| Δ22-36 | deletion of 14 internal residues | >2000 | 1 |

*Reactivity of a series of mutant OM molecules captured by mAb OM3 with biotinylated OM1 or OM2 was assessed. Serum-free conditioned media from COS cells transfected with a series of plasmids containing various insertions, deletions, or substitutions listed below were tested.

Structural analysis of the OM molecule indicated the presence of a strongly amphipathic/amphiphilic region near the C-terminus from aa168–196. The OM1 and OM2 antibodies were tested for their binding to a series of mutants which had sequential C-terminal deletions. Both OM1 and OM2 were capable of detecting OM, with high affinity, from mutants which had sequential C terminal amino acid deletions up to aa 186 (as indicated by the high concentration of protein bound). For the Δ185–227 C terminal deletion mutant, both antibodies bound with lower affinity; the binding level of OM2, the neutralizing antibody, was lower than that of OM1. Binding activity of both antibodies was completely lost in the C-terminal deletion mutant Δ184–227. A series of mutants of the amphiphilic region with residue changes from either hydrophobic or hydrophilic to neutral amino acids presented a more complex pattern of antibody binding. Of the three phenylalanine to glycine changes, only that at position 176 resulted in complete loss of binding by both antibodies, while the change at 184 reduced the binding of the neutralizing antibody OM2, but not OM1. The substitution from phenylalanine to glycine at residue 169 had no effect on the binding of either antibody. Two separate proteins, H174G and H178G, with alterations of hydrophilic hisitidines to glycine at positions 174 and 178, respectively, were bound with high affinity by both OM1 and OM2.

Two intramolecular disulfide bonds exist in the native Oncostatin M molecule. The C6–C127 disulfide bond did not affect the local tertiary structure(s) of the OM1 and OM2 epitopes, since antibody binding was not reduced when the cysteine at position 6 was changed to serine. Elimination of both disulfide bonds (C6S/C167S) destroyed the epitopes of both antibodies, presumably by causing global misfolding of the molecule.

Two mutant OM molecules, Δ44–47, and Δ22–36, were informative in discriminating the binding requirements of antibodies OM1 and OM2. These deletion mutants were bound by OM1, the non-neutralizing antibody, but not by OM2, the neutralizing antibody. A schematic model of the functionally important regions of the Oncostatin M molecule determined with OM2, and with the mapping of OM3 and OM4 epitopes is presented in FIG. 7.

7. DEPOSIT OF MICROORGANISMS

The following cell lines have been deposited with the American Type Culture Collection, Rockville, Md., and have been assigned the listed accession numbers:

| Cell Line | Accession Number | Antibody |
|---|---|---|
| 11R2F8.9 | ATCC HB 10398 | OM2 |
| 12R13D7.2 | ATCC HB 10396 | OM3 |
| 1R10F11.34.16 | ATCC HB 10397 | OM1 |

The present invention is not to be limited in scope by the cell lines deposited since the deposited embodiments are intended as single illustrations of individual aspects of the invention, and any cell lines or antibodies which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. A monoclonal antibody, the epitope combining site of which competitively inhibits essentially all of the epitope binding of monoclonal antibody OM2 produced by hybridoma HB 10398, as deposited with the ATCC.

2. An Fab, F(ab')$_2$ or Fv fragment of the monoclonal antibody of claim 1.

3. The monoclonal antibody of claim 1 conjugated to a signal-generating compound capable of producing a detectable signal.

4. The monoclonal antibody of claim 3 wherein the signal-generating compound is selected from the group consisting of a fluorescer, radiolabel, a chromophore and an enzyme.

5. The monoclonal antibody fragment of claim 2, conjugated to a signal-generating compound capable of producing a detectable signal.

6. The monoclonal antibody fragment of claim 5 wherein the signal-generating compound is selected from the group consisting of a fluorescer, a radiolabel, a chromophore and an enzyme.

7. A monoclonal antibody, the epitope combining site of which competitively inhibits essentially all of the epitope binding of monoclonal antibody OM3 produced by hybridoma HB 10396, as deposited with the ATCC.

8. An Fab, F(ab')$_2$ or Fv fragment of the monoclonal antibody of claim 7.

9. The monoclonal antibody of claim 7 conjugated to a signal-generating compound capable of producing a detectable signal.

10. The monoclonal antibody of claim 9 wherein the signal-generating compound is selected from the group consisting of a fluorescer, a radiolabel, a chromophore and an enzyme.

11. The monoclonal antibody fragment of claim 8 conjugated to a signal-generating compound capable of producing a detectable signal.

12. The monoclonal antibody fragment of claim 11 wherein the signal-generating compound is selected from the group consisting of a fluorescer, a radiolabel, a chromophore and an enzyme.

13. A monoclonal antibody, the epitope combining site of which competitively inhibits essentially all of the epitope binding of monoclonal antibody OM1 produced by hybridoma HB 10397, as deposited with the ATCC.

14. An Fab, F(ab')$_2$ or Fv fragment of the monoclonal antibody of claim 13.

15. The monoclonal antibody of claim 13 conjugated to a signal-generating compound capable of producing a detectable signal.

16. The monoclonal antibody of claim 15 wherein the signal-generating compound is selected from the group consisting of a fluorescer, a radiolabel, a chromophore and an enzyme.

17. The monoclonal antibody fragment of claim 14 conjugated to a signal-generating compound capable of producing a detectable signal.

18. The monoclonal antibody fragment of claim 17 wherein the signal-generating compound is selected from the group consisting of a fluorescer, a radiolabel, a chromophore and an enzyme.

19. Hybridoma cell line OM2 as deposited with the ATCC having accession number HB 10398.

20. Hybridoma cell line OM3 as deposited with the ATCC having accession number HB 10396.

21. Hybridoma cell line OM1 as deposited with the ATCC having accession number HB 10397.

22. The monoclonal antibody OM2 produced by hybridoma HB 10398 as deposited with the ATCC.

23. The monoclonal antibody OM3 produced by hybridoma HB 10396 as deposited with the ATCC.

24. The monoclonal antibody OM1 produced by hybridoma HB 10397 as deposited with the ATCC.

* * * * *